United States Patent
Ciamacco, Jr. et al.

[19]

[11] Patent Number: 5,938,582
[45] Date of Patent: Aug. 17, 1999

[54] RADIATION DELIVERY CENTERING CATHETER

[75] Inventors: Sam Ciamacco, Jr., San Diego; Mark L. Stiger, El Cajon; Michael A. Mohn, Jr., San Diego, all of Calif.

[73] Assignee: Medtronic, Inc., Minneapolis, Minn.

[21] Appl. No.: 08/938,780

[22] Filed: Sep. 26, 1997

[51] Int. Cl.$^6$ .................................................. A61N 5/00
[52] U.S. Cl. ................................................................ 600/3
[58] Field of Search ............................................ 600/1–8

[56] References Cited

U.S. PATENT DOCUMENTS

| | | | |
|---|---|---|---|
| 3,324,847 | 6/1967 | Zoumboulis | 128/62 |
| 4,660,571 | 4/1987 | Hess et al. | 128/784 |
| 4,699,147 | 10/1987 | Chilson et al. | 128/642 |
| 4,819,618 | 4/1989 | Liprie | 600/7 |
| 5,141,487 | 8/1992 | Liprie | 600/7 |
| 5,199,939 | 4/1993 | Dake et al. | 600/3 |
| 5,213,561 | 5/1993 | Weinstein et al. | 600/7 |
| 5,295,995 | 3/1994 | Kleiman | 606/194 |
| 5,322,499 | 6/1994 | Liprie | 600/8 |
| 5,503,613 | 4/1996 | Weinberger | 600/3 |
| 5,540,659 | 7/1996 | Teirstein | 604/104 |
| 5,554,119 | 9/1996 | Harrison et al. | 604/96 |
| 5,616,114 | 4/1997 | Thornton et al. | 600/3 |
| 5,643,171 | 7/1997 | Bradshaw et al. | 600/1 |
| 5,730,698 | 3/1998 | Fischell et al. | 600/3 |

FOREIGN PATENT DOCUMENTS

| | | |
|---|---|---|
| 0 688 580 A1 | 6/1994 | European Pat. Off. . |
| 0 686 342 A1 | 10/1994 | European Pat. Off. . |
| WO 93/04734 | 3/1993 | WIPO . |
| WO 94/25106 | 11/1994 | WIPO . |
| WO 95/26681 | 10/1995 | WIPO . |
| WO 96/10436 | 4/1996 | WIPO . |
| WO 96/13303 | 5/1996 | WIPO . |

OTHER PUBLICATIONS

*Balloon Catheters for Percutaneous Insertion into the Vascular System*, Department of Diagnostic Roentgenology, Bjorn Nordenstrom, M.D.
*New Instruments for Catheterization and Angiocardiography*, Bjorn Nordenstrom, M.D., Radiology, vol. 85, Jul.–Dec. 1965.

Primary Examiner—John P. Lacyk
Attorney, Agent, or Firm—John R. Duncan; Dianne Plunkett Latham; Harold R. Patton

[57] ABSTRACT

An apparatus for centering a radiation delivery device at a selected location in a body vessel such as a coronary artery. An elongated catheter is insertable into the body vessel until the catheter head is in the desired position. The catheter has a guidewire lumen, inflation lumen and treatment lumen running lengthwise. The catheter head includes an expandable mechanism for engaging the vessel internal wall with the treatment lumen centered in the vessel. At least one channel is provided extending past the expandable mechanism so that a fluid, such as blood, can perfuse past the catheter head. A radiation delivery device, such as a wire having a radiation source at the distal end can be inserted into the treatment lumen to uniformly irradiate the vessel wall at the selected location.

12 Claims, 7 Drawing Sheets

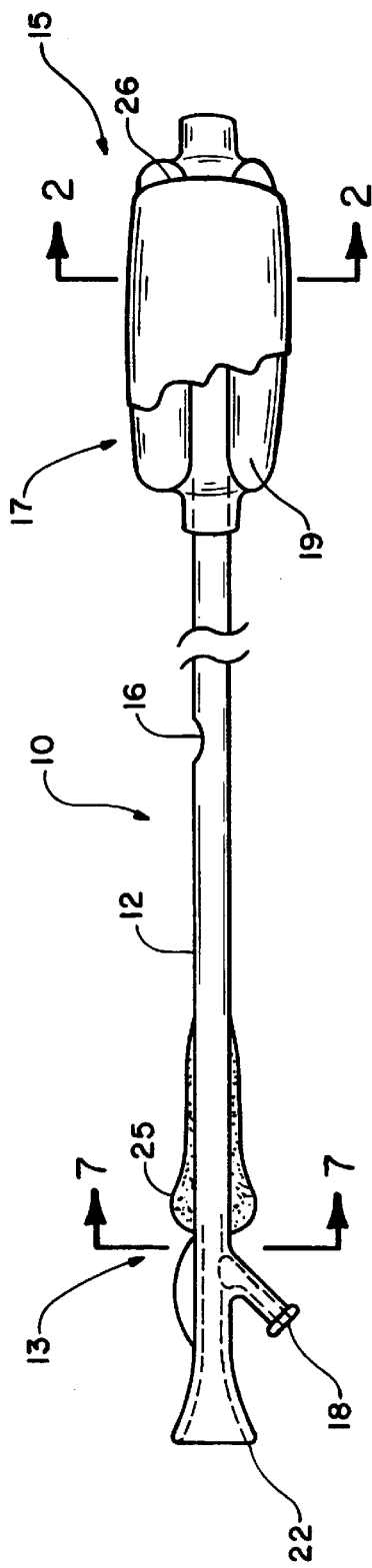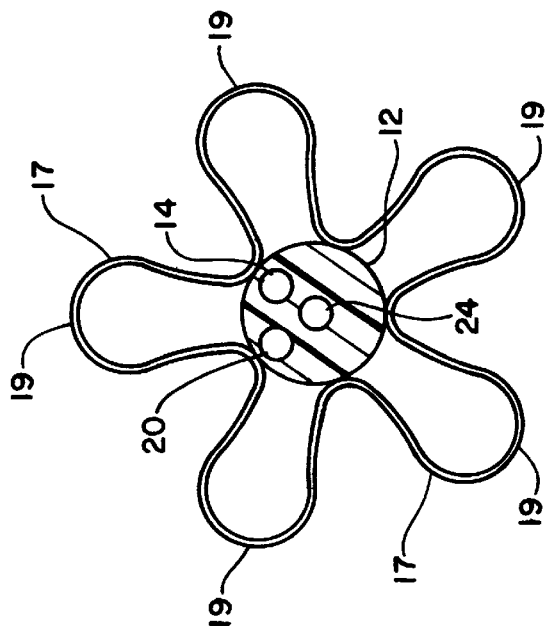
FIGURE 1
FIGURE 2
FIGURE 3

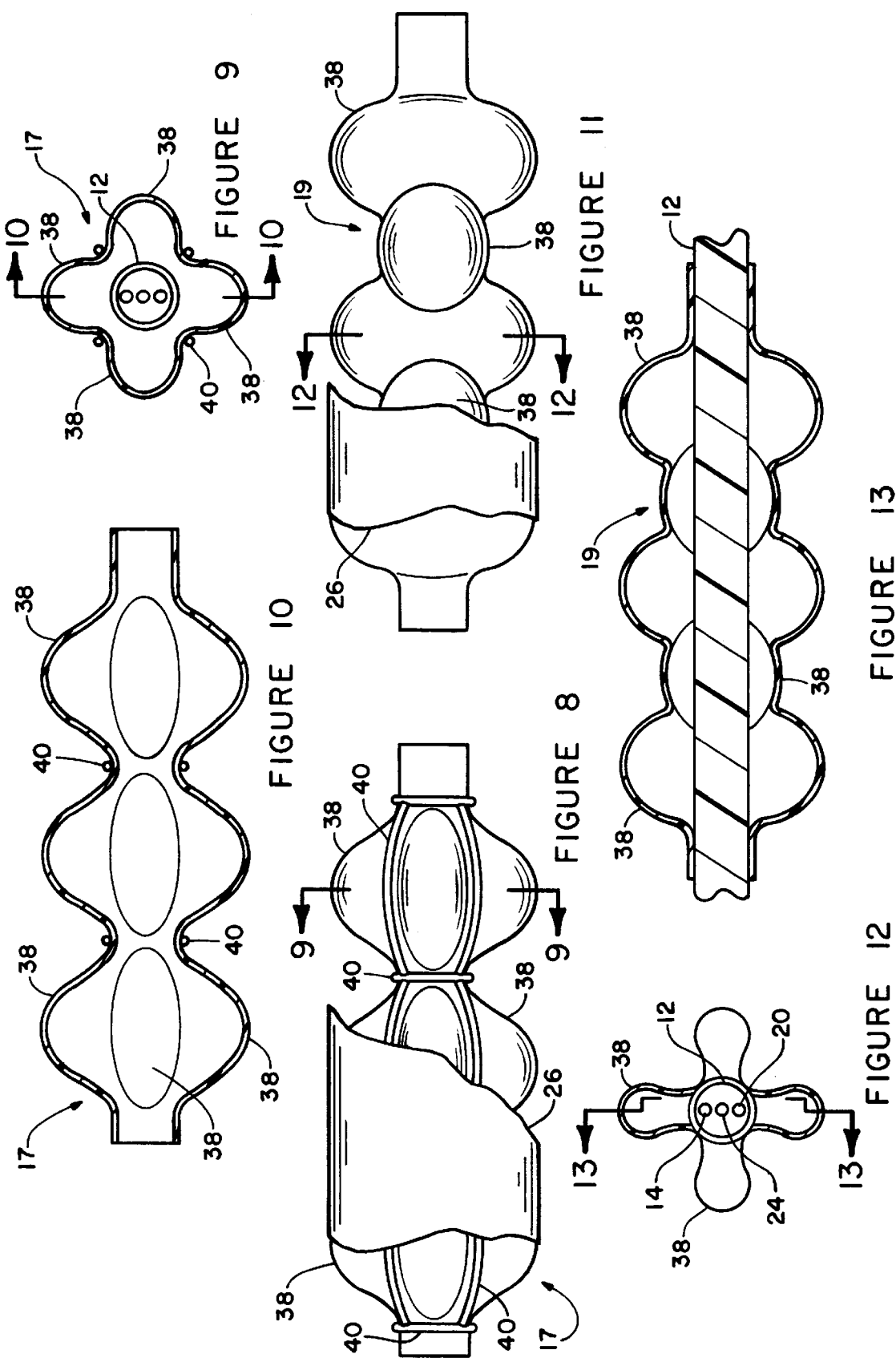

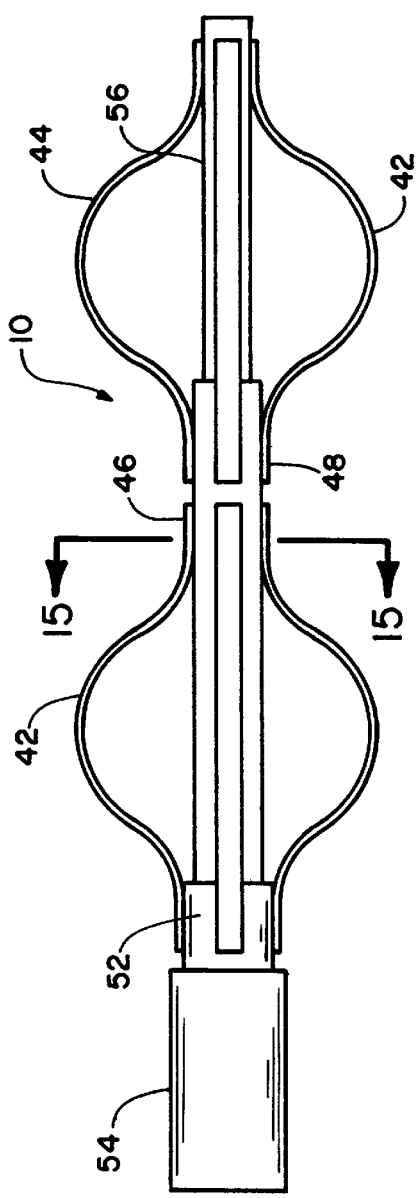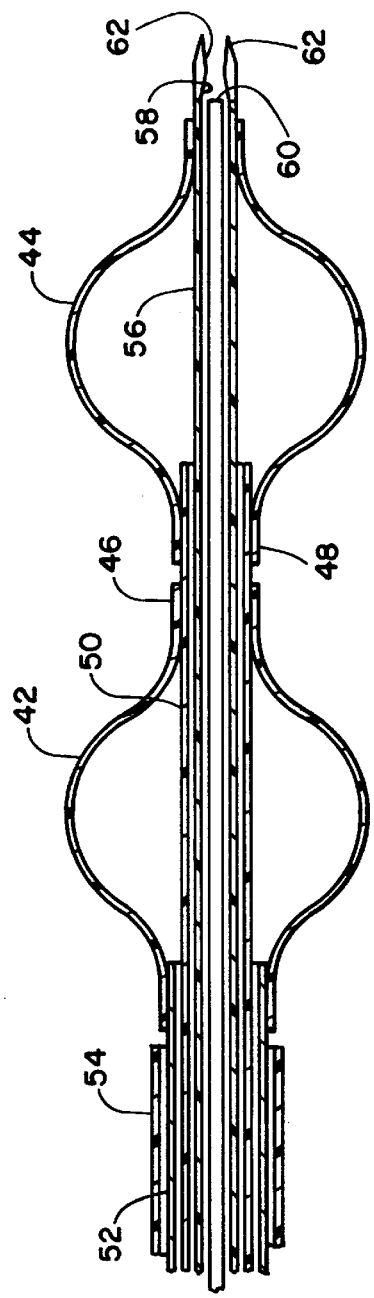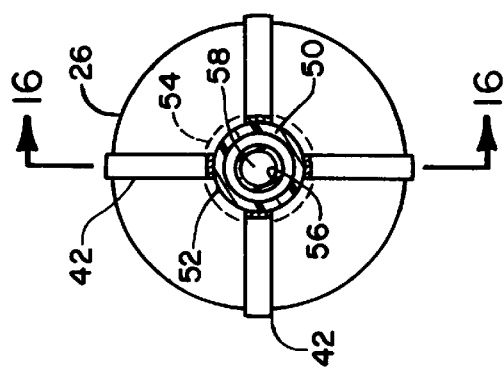

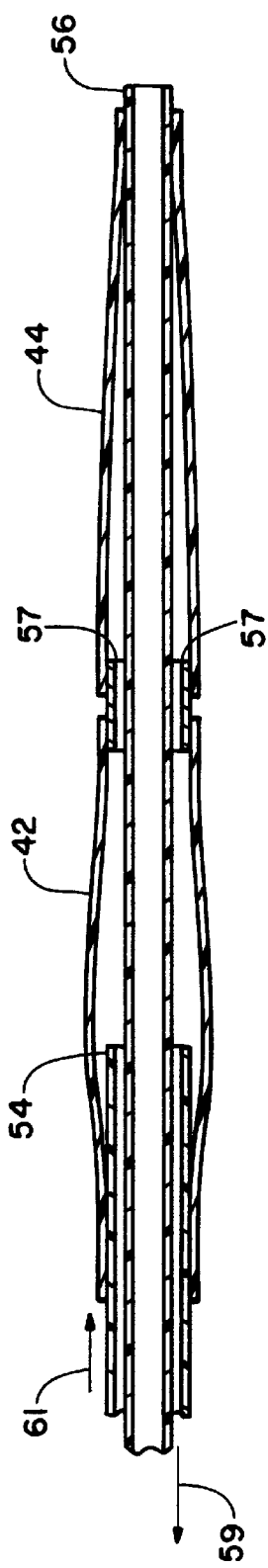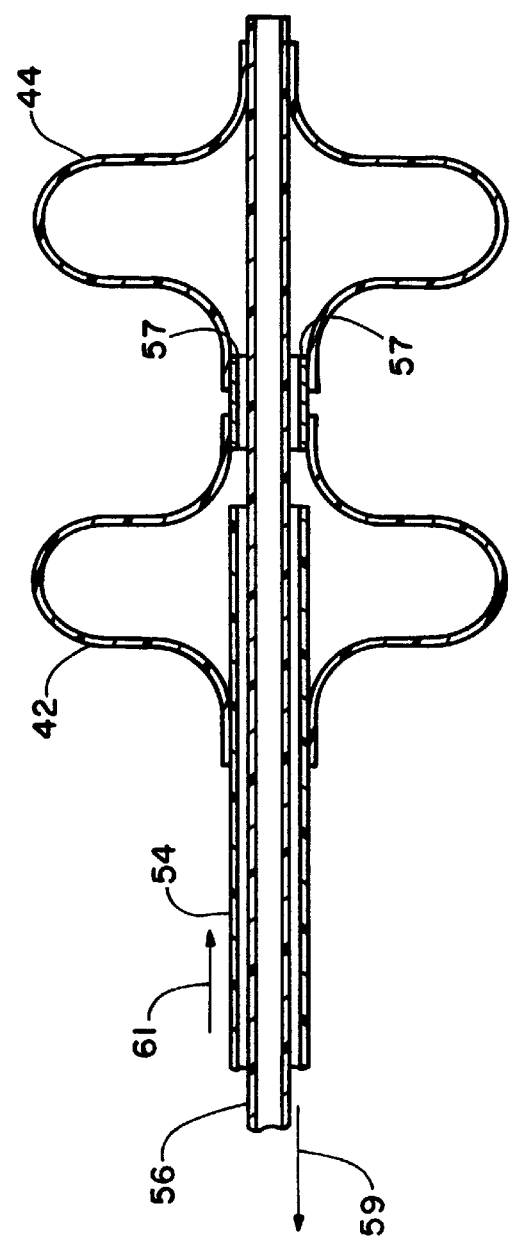

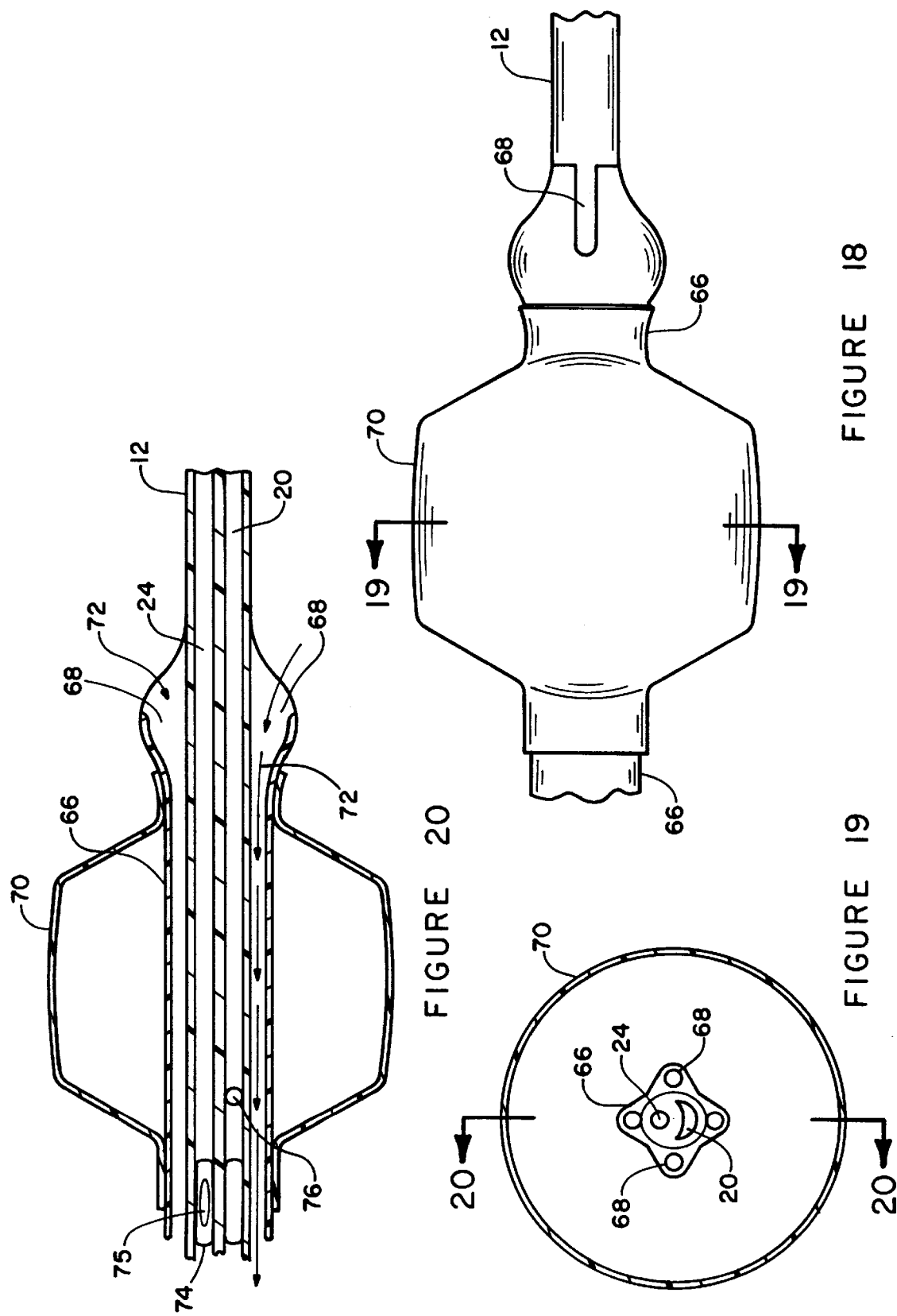

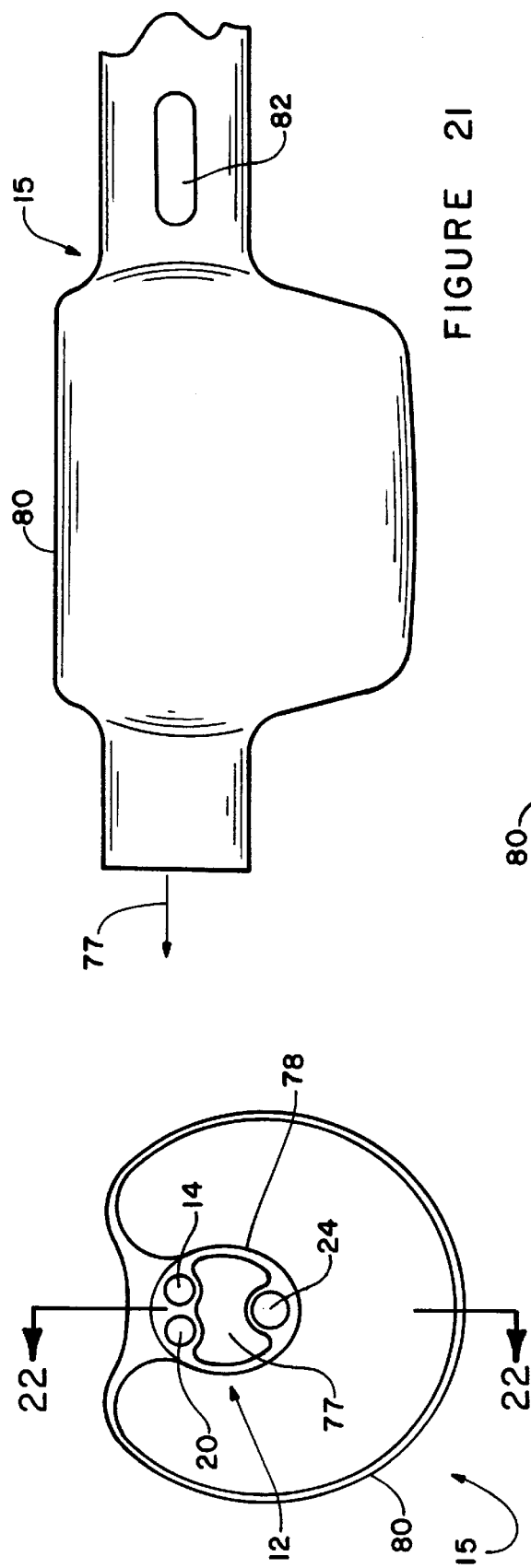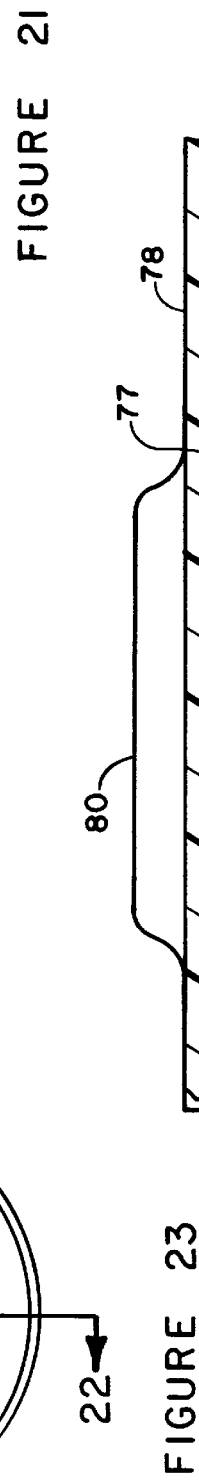

RADIATION DELIVERY CENTERING CATHETER

FIELD OF THE INVENTION

This invention relates to apparatus for supporting a radiation emitting source in a body lumen such as a coronary artery which will center the source in the artery for uniform treatment of the lumen walls. In addition, the apparatus will allow fluid perfusion past the apparatus during a radiation treatment.

BACKGROUND OF THE INVENTION

Percutaneous transluminal coronary angioplasty (PTCA) is often used to reduce arterial build-up of cholesterol fats or atherosclerotic plaque in coronary arteries. Typically a guidewire is inserted into an incision in an artery and is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. While the stenosis or occlusion is greatly reduced, many patients experience a reoccurrence of the stenosis over a relatively short period. Researchers have found that angioplasty or placement of a stent in the area of the stenosis irritates the blood vessel causing rapid reproduction of the inner layer of blood vessel cells and restenosis through a mechanism called hyperplasia. It has been found that irradiating the blood vessel walls at the point of the stenosis will reduce or prevent hyperplasia. Precise control over the amount of radiation is important, since insufficient radiation will not prevent hyperplasia and excessive radiation can damage the blood vessel.

For other diagnostic or treatment purposes, it is also often desirable to introduce a small radiation source into a body vessel such as a coronary artery. Simply inserting a wire with a source secured in the wire at or near the distal end is effective in some cases. However, the wire will tend to lie along one side of the vessel, so that the near side receives significantly more radiation than the opposite, distant side. The near side could receive excessive, damaging, radiation exposure before the opposite side received the desired dose. Such a non-centering, wire-carried, radiation source is shown by Dake et al. in U.S. Pat. No. 5,199,939 and Bradshaw in U.S. Pat. No. 5,643,171. Therefore, it would be highly desirable to provide a radiation delivery system that would assure that the source is centered in the vessel.

Zoumboulis, in U.S. Pat. No. 3,324,847, describes a catheter having a spherical inflatable chamber adjacent the catheter distal end. A fluid containing a radioactive material such as radioactive iodine is pumped into the chamber, inflating the chamber and treating the vessel walls with ionizing radiation. The chamber will stop blood flow, so can be inflated for only a short period. Further, precisely controlling radiation exposure and fully draining the chamber to end treatment are very difficult.

A wire carrying a radioactive source could be inserted through a catheter lumen to the balloon location. The balloon would approximately center the source in the artery. However, since many guide wires extend mainly alongside the balloon catheter and balloons generally expand somewhat unevenly, the source would not be precisely centered. Further, irradiating a segment of an artery or the like generally requires some time, typically from about 3 to 45 minutes. Since a conventional angioplasty balloon substantially shuts off blood flow through the artery, treatment can be conducted for only short periods before damage from lack of blood flow becomes significant.

Liprie, in international patent application publication number WO95/26681 describes a device for treating a vessel occlusion with radiation in which a ribbed balloon catheter is inserted into a body vessel and inflated to provide perfusion between the ribs and a wire carrying a radiation source is inserted into a lumen extending into the balloon area. This positions the radiation source generally near the center of the vessel. However, as disclosed, the lumen has a much greater inside diameter than the outside diameter of the source wire, so that the source will generally be off center, in contact with the lumen wall. This will result in uneven irradiation of the vessel wall on opposite sides.

Other ribbed arrangements, using a double spiral rib or circumferential ribs are disclosed by Bradshaw et al. in U.S. Pat. No. 5,643,171 for centering a treatment lumen in a body vessel. While useful, the lobes may not provide precise centering, especially if the treatment wire is not a good fit in the lumen.

Teirstein in U.S. Pat. No. 5,540,659 describes a series of centering wire loops for centering a wire-carried radiation source in a body vessel. The generally oval shape of the wire loops and the complexity of inserting and removing the loop device make this arrangement less than fully effective. Teirstein also shows in his FIGS. 5 and 6 an embodiment using flexible wires that can be expanded away from a central catheter. However, the use of a single set of wires extending from the distal to proximal ends of the treatment zone will tend to allow the catheter to tilt relative to the wires. Also this system does not allow the use of multiple sets of expansion wires that could be opened independently.

A series of approximately spherical balloons are used to center a radiation source in the arrangement of Verin et al. as disclosed in European patent application number 94109858.4. Although the source is centered in the vessel, lack of perfusion of blood past the site would permit only very short treatment times.

Thus, there is a continuing need for improved devices for carrying a radiation source to a desired site along a body vessel that can be easily and accurately inserted into and removed from even very small vessels and which accurately center the source in the vessel while permitting effective perfusion so that treatment can be conducted over reasonably long periods.

SUMMARY OF THE INVENTION

The above-noted problems, and others, are overcome in accordance with this invention by an apparatus for centering a radiation delivery device in a body vessel which basically comprises an elongated tubular catheter assembly having a catheter head at a distal end and at least one lumen extending therethrough, means for inserting the catheter head into a body vessel to a treatment location, the catheter head including means for centering the lumen in the body vessel, means for inserting a radiation delivery device into the lumen to the treatment location with the device substantially filling the centered lumen and means for permitting perfusion past the catheter head.

Any conventional insertion means, such as a conventional catheter assembly may be used for introducing the catheter head into the vessel and locating the head at a treatment location. Typically, the catheter assembly includes a manifold through which the catheter can be slid into the body vessel via a slit in the vessel. Typically, the body vessel could be an artery where a coronary artery is to be treated.

The radiation delivery device is typically a wire bearing the radioactive material at the distal end. A conventional shielding tube to cover the radioactive material at all times except during the treatment period may be used, if desired.

The cooperating centering means and perfusion means may be any of several different embodiments of devices for expanding the diameter of the catheter head into contact with the wall of the body vessel with the lumen centered in the catheter head while permitting blood flow past the device. Other lumens may be provided through the length of the catheter for receiving a guide wire, as a passage for a fluid, etc.

In a first embodiment, a combined centering and perfusion means is provided at the catheter head, comprising at least three equal sized, spaced, elongated, outwardly extending inflatable lobes along the catheter head. The lobes may extend for a predetermined distance along lines parallel to the catheter center line or may be arranged around the catheter in a spiral arrangement.

A central lumen is provided in said catheter head, located so as to be substantially centered in a body vessel after the lobes are inflated. A second, non-centered, lumen is provided through the catheter and communicates with the lobes for passage of an inflating fluid. A third lumen may be provided for passage of a guide wire or the guide wire could use the inflation lumen, as desired.

The lobes may have any suitable transverse cross section. In one preferred configuration, the lobes have a transverse cross section similar to a rounded isosceles triangle with the triangle base at the catheter. In another preferred configuration, the lobe transverse cross section is narrower near the catheter and wider at the lobe tip, having a generally "mushroom" shaped cross section.

In a second basic embodiment, a plurality of spaced, usually equally sized, outwardly extending knobs are provided along said catheter, each knob having a base against the catheter. When inflated with a fluid, the knobs extend away from the catheter equal distances. In a body vessel, the knobs contact the vessel wall, centering the catheter and allowing flow of blood between the knobs and thus past the catheter head. A central lumen is provided in the catheter for receiving an elongated radiation device, such as a wire bearing a quantity of radioactive material. In one preferred version of this configuration, a plurality of radial sets of three or more knobs are arranged along the catheter. The knobs in succeeding sets may be longitudinally aligned with knobs in the preceding set or may be sequentially staggered, as desired. In another preferred version of this configuration, knob sets are made up of pairs of knobs extending outwardly on opposite sides of the catheter. Succeeding pairs of knobs lie at from about 60 to 120° to the orientation of the preceding set. Optimally, each succeeding set is rotated about 90° to the orientation of the preceding set.

A third basic embodiment includes a plurality of torsion bars along the catheter movable from an storage (or insertion/removal) position where the bars are substantially straight and positioned along the catheter outer surface and a deployed position where they are arched outwardly a uniform distance into contact with the inner wall of a body vessel, so as to center the catheter in the vessel. The bars are preferably quite narrow, so that an especially large transverse area is provided for perfusion.

While a single radial set of torsion bars could be used, the torsion bars are preferably arranged in two sets of at least three bars. One end of each bar is secured to the catheter, with the opposite ends of the bars in the first set secured to a longitudinally movable first tube and the opposite ends of the bars in the second set are secured to a second longitudinally movable tube. When the two tubes are moved longitudinally to bring bar ends toward each other, the bars will bulge outwardly, while moving the bar ends away from each other will cause them to straighten. The bars may be formed from any suitable material, such as metals, plastics, etc. and are preferably preset in the bulged configuration.

A forth basic embodiment has a central catheter core with a central treatment lumen and an inflation lumen. A balloon surrounds the core in communication with the inflation lumen to inflate and deflate the balloon, with the treatment lumen centered in the balloon when the balloon is inflated. A plurality of open ended tubes in the core extend past both distal and proximal ends of the balloon, allowing fluid perfusion past the balloon when the balloon is inflated.

A fifth basic embodiment includes a catheter having a large longitudinal perfusion lumen, with a treatment lumen at one side of the perfusion lumen and other lumens (e.g. guidewire lumen, inflation lumen) on the opposite side. A balloon is secured to the catheter adjacent to the other lumens such that the treatment lumen will be centered in the balloon when the balloon is inflated via a connection to the inflation lumen. The inflation lumen is open to the body vessel at both ends, beyond the distal and proximal ends of the balloon, allowing fluid perfusion therethrough when the balloon is inflated and in contact with the inner wall of a body vessel.

In each of these embodiments, a treatment lumen is positioned at the center of a body vessel in which the catheter assembly is inserted and the centering means activated. The treatment device is a sliding fit in the treatment lumen, substantially filling the treatment lumen, avoiding any variation in treatment of the vessel wall that would occur is the treatment device were a loose fit in a central lumen of greater diameter and could lie against one side of the large lumen.

With each of the embodiments, a sheath may be provided over the expandable centering means, to prevent or reduce entrance of body vessel material into the perfusion channels that would reduce perfusion effectiveness.

BRIEF DESCRIPTION OF THE DRAWINGS

Details of the invention, and of preferred embodiments thereof, will be further understood upon reference to the drawing, wherein:

FIG. 1 is a side elevation of a catheter assembly including the centering/perfusion means of this invention;

FIG. 2 is a transverse section view, taken on line 2—2 in FIG. 1;

FIG. 3 is a transverse section view of an alternate embodiment to that shown in FIG. 2, taken on a line corresponding to line 2—2 in FIG. 1 without sheath 26;

FIG. 8 is a side elevation view of another catheter centering/perfusion embodiment;

FIG. 9 is an end elevation view of the embodiment of FIG. 10;

FIG. 10 is a axial section view taken on line 10—10 in FIG. 9 shown without the catheter 12;

FIG. 11 is a side elevation view of another catheter centering/perfusion embodiment;

FIG. 12 is a transverse section view taken on line 12—12 in FIG. 11;

FIG. 13 is a axial section view taken on line 13—13 in FIG. 12;

FIG. 14 is a side elevation view of another catheter centering/perfusion embodiment having expanded torsion bars;

FIG. 15 is a transverse section view taken on line 15—15 in FIG. 14;

FIG. 16 is an axial section view taken on line 16—16 in FIG. 15;

FIG. 17a shows an axial section through another torsion bar embodiment in the unexpanded position;

FIG. 17b shows an axial section through the torsion bar embodiment of FIG. 17a in the fully expanded position;

FIG. 18 is a side elevation view of another catheter centering/perfusion embodiment;

FIG. 19 is a transverse section view taken on line 19—19 in FIG. 18;

FIG. 20 is an axial section view taken on line 20—20 in FIG. 19;

FIG. 21 is a side elevation view of another catheter centering/perfusion embodiment;

FIG. 22 is an axial section view through the embodiment shown in FIG. 21; and

FIG. 23 is a transverse section view in FIG. 21.

DETAILED DESCRIPTION OF PREFERRED EMBODIMENTS

Figure 7:
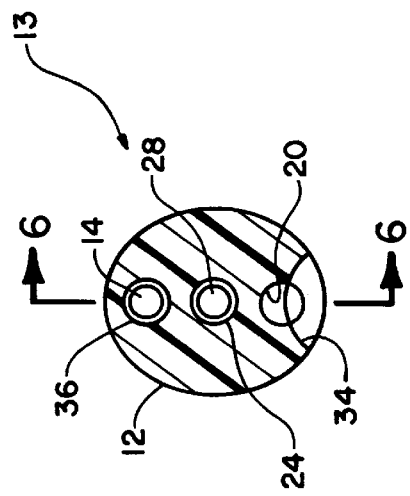
FIG. 7 is a transverse section view taken on line 7—7 in FIG. 1.

Referring to FIGS. 1–3, there is seen a first preferred embodiment of a catheter for use in irradiating a predetermined section of a body vessel, which includes a means for centering an irradiation treatment device within a catheter in a body vessel and for allowing fluid perfusion past the treatment site.

FIG. 1 shows an entire catheter assembly 10. The catheter 12 is formed from a flexible plastic and includes a manifold 13 at the proximal end and a catheter head 15 at the distal end. Several longitudinal lumens extend through catheter 12 from manifold 13 to head 15, as seen in FIGS. 2 and 3. Typically the lumens and associated entrance ports include a guide wire lumen 14 having an entrance port 16, an inflation port 18 to furnish inflating media to the catheter balloon lobes 19 via inflation lumen 20 and a treatment device port 22 into a treatment lumen 24. A stress relief collar 25 may be provided adjacent to manifold 13. A sleeve 26 may be placed over balloon 17 to prevent vessel wall material entering between balloon lobes and restricting perfusion between those lobes.

As seen in FIGS. 2 and 3, balloon 17 may have three or more spaced lobes 19 each running longitudinally parallel to the catheter centerline. Balloon 17 may have any suitable number of lobes, with at least three providing the best results. Balloon lobes 19 in these embodiments have an upstanding shape with a rounded end or a generally rounded isosceles triangle form.

While it is desirable that treatment lumen 24 be precisely centrally located, being slightly off center as seen in the radial lumen arrangement of FIG. 2 is sometimes satisfactory. As seen in FIG. 3, the three radially arranged lumens running through catheter 12 could be offset slightly so that treatment lumen 24 is precisely centered and the other lumens offset. For optimally uniform radiation treatment of body vessel walls, treatment lumen 24 should be at the precise center of the catheter 12, as seen in the arrangement of FIGS. 3 and 7.

Figure 5:
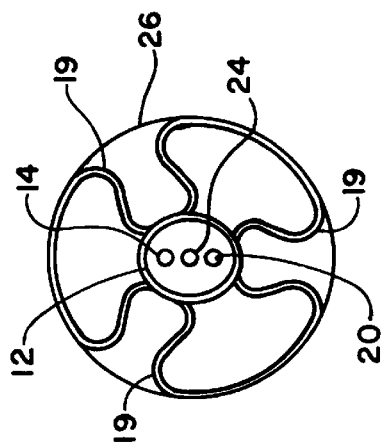
FIG. 5 is a transverse section view, taken on line 5—5 in FIG. 4.
Figure 4:
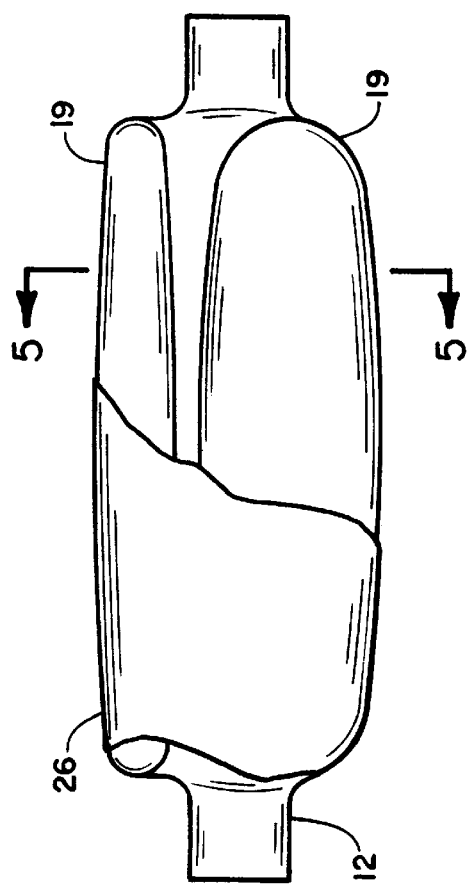
FIG. 4 is a side elevation view, partly cut away, of an alternate catheter head embodiment.

FIGS. 4 and 5 show another embodiment of the apparatus. The balloon here has lobes 19 with a cross section that is much wider near the lobe tip than adjacent to catheter 12, in a generally "mushroom" cross sectional shape. This configuration is advantageous in producing higher dilatation force without collapse of sheath or sleeve 26. In order to precisely locate treatment lumen 24 at the center of catheter 12 while balancing forces, the three lumens are arranged in a straight line with treatment lumen 24 in the center.

Figure 6:
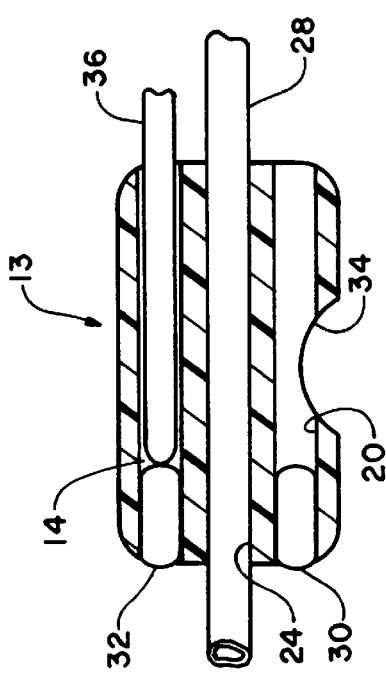
FIG. 6 is a axial section view through the proximal manifold end, taken on line 6—6 in FIG. 7.

FIGS. 6 and 7 show details of the manifold 13, with FIG. 7 being taken on line 7—7 in FIG. 1. A treatment device 28, typically a flexible wire carrying a quantity of radioactive material, is inserted through treatment port 22 (FIG. 1) to the treatment site. If desired, treatment device may be carried in a radiation absorbing shield tube (not shown) to the treatment site, then the shield tube can be withdrawn so that the walls of the vessel can be irradiated, after which the tube is moved over the radiation source and the treatment device and shield tube can be withdrawn together. During irradiation, which may require a relatively long period, fluids such as blood can perfuse between the lobes 19.

Inflation lumen 20 and guide wire lumen 14 are plugged at the proximal end of catheter 12 by plugs 30 and 32, respectively. The side of inflation lumen 20 is skived at 34 to permit inflating fluid to flow into lobes 19. Stylet 36 extends through guide wire lumen 14 and abuts plug 32 for support.

Another embodiment of the apparatus is shown in FIGS. 8–10. Here, balloon 17 is in the form of a pattern of radial sets of knobs 38. As seen in the end view of FIG. 9, in the arrangement shown, four spaced knobs 38 are provided in each radial set. For clarity, the axial section view of FIG. 10 omits catheter 12 so that the far side knobs 38 can be seen.

While any suitable number of knobs 38 may be used, for best results three or more knobs are preferred. Any suitable number of sets of knobs 38 may be used, depending upon the desired length of the treatment zone. While each knob may have any suitable shape, a rounded isosceles triangle with the base against catheter 12 is generally preferred. If desired a sheath or sleeve 26 (shown partly cut away in FIG. 8) may be placed over the knob array to prevent body vessel material from intruding into the perfusion space between knobs 38.

In order to stabilize the knob configuration and aid in uniform centering, reinforcing bands 40 may be placed around the base of each knob 38 and circumferentially around the balloon between knob sets, as best seen in FIGS. 8 and 9. Bands 40 may be formed from any suitable material, such as metal or plastic wires, cords, narrow strips, etc., any of which could be adhesively bonded to balloon 12 if desired.

In order to reduce or prevent intrusion of body vessel material into the perfusion space, a sleeve 26 (shown partly cut away) may be provided.

Another embodiment of the centering and perfusion apparatus, again using a plurality of outwardly projecting knobs 38, is shown in FIGS. 11–13. Here each set of knobs 38 consists of two knobs on opposite sides of catheter 12. The series of sets of knobs 38 are relatively rotated, in the arrangement shown, each succeeding set is rotating about 90° to the preceding set. If desired, each succeeding set can be rotated at any desired angle to the preceding set within the range of from about 60° to 120°. In order to reduce or prevent intrusion of body vessel material into the perfusion space, a sleeve 26 (shown partly cut away in FIG. 11) may be provided.

Another embodiment of the apparatus for centering a radiation delivery device in a body vessel while permitting perfusion that uses a torsion bar centering arrangement is illustrated in FIGS. 14–17.

FIG. 14 shows the apparatus in the partially expanded, centered, position. FIGS. 15 and 16 are section views showing details of the central part of this assembly. As seen in FIG. 14, a plurality of first torsion bars 42 and second torsion bars 44 are evenly spaced around the exterior of catheter assembly 10. Any suitable number of torsion bars may be used, preferably at least three spaced torsion bars. Multiple sets of torsion bars are especially useful in treating long lesions.

The adjacent or approximately abutting ends 46 and 48, respectively, of torsion bars 42 and 44 are fastened, such as by adhesive bonding, to a central tube 50. The second ends of torsion bars 42 are fastened to an outer tube 52 slidable over central tube 50. Outer tube 52 is slidably contained within a sleeve 54. The second ends of torsion bars 44 are fastened to an inner tube 56 that is slidable within central tube 50. Thus, as outer tube 52 is pushed over central tube 50 (or, conversely, central tube 50 is pulled back into outer tube 52) torsion bars 42 will move from the unexpanded position to the expanded position shown in FIG. 14. Preferably, torsion bars 42 and 44 are shaped to naturally seek the unexpanded position and are expanded against that tension when moved to the expanded position. Similarly, when inner tube 56 is pulled back into central tube 50 (or central tube 50 is pushed over inner tube 56), torsion bars 44 will expand to the position shown in FIGS. 14 and 16. These various tubes may be moved manually or by any suitable mechanism. Torsion bar sets 42 and 44 may be moved simultaneously or individually, as desired.

As best seen in FIGS. 15 and 16, central lumen 58 functions as both a guide wire lumen and a treatment lumen for receiving a radiation delivery device 60. Distal tip 62 of lumen 58 (FIG. 16) is narrowed so that a relatively thin guide wire (not shown) can pass through the tip and the catheter can be moved along the guide wire to emplace the catheter in a conventional manner. The radiation delivery device 60 has a diameter substantially filling central lumen 58, being a sliding fit therein, so that device 60 cannot pass by distal tip 62. Since the delivery device 60 is a snug fit in central lumen 58, the delivery device will be precisely centered in the body vessel when the catheter 12 is centered, which would not be the case if the delivery device 60 were a loose fit and could move from side to side of central lumen 58.

FIGS. 17a and 17b show another embodiment of a torsion bar type assembly wherein both sets of torsion bars 42 and 44 are moved together by a single actuating tube 56 secured to the distal end of torsion bars 44 and forming central lumen 58. FIG. 17a shows the assembly in the substantially unexpanded state and FIG. 17b shows the assembly in the fully expanded state.

In FIG. 17a, torsion bars 42 and 44 are substantially parallel to the inner tube 56. The ends of torsion bars 42 are bonded to sleeve 54 at proximal ends and to ring 57 at distal ends. Torsion bars 44 are bonded to ring 57 at proximal ends and to inner tube 56 at distal ends. Torsion bars 42 and 44 are preferably two independent sets, although in some cases continuous bars could extend from sleeve 54 to tube 56, bonded at an intermedial radial line to ring 57. Ring 57 has the same diameter as sleeve 54. Sleeve 54, torsion bars 42 and 44, ring 57 could be formed of one piece.

The torsion bars are moved to the expanded position shown in FIG. 17b by moving sleeve 54 in the direction indicated by arrow 61 and/or moving inner tube 56 in the direction indicated by arrow 59. This movement may be accomplished manually or mechanical, as desired, from the ends of tube 56 and sleeve 54 at manifold 13.

A further embodiment is illustrated in FIGS. 18–20. Here, catheter 12 is surrounded by a core or body 66 having four longitudinal perfusion flow channels 68 therethrough. An inflatable balloon 70 surrounds body 66 to center core 66 within the balloon. The ends of perfusion channels 68 extend beyond the proximal and distal balloon ends, permitting perfusion as indicated by arrows 72. a central treatment lumen 24 is configured to receive a radiation delivery device in a sliding fit. The distal end of central treatment lumen is closed by a plug 74 to prevent passage of a delivery device beyond the balloon region. An inflation lumen 20 is provided for directing balloon inflation fluid into balloon 70 through opening 76 between the balloon and the inflation lumen. To more precisely center core 66 in the body vessel, a multiple knob-like balloon, a spiral balloon or torsion bars of the sort described above could be used, if desired. A radio-opaque marker 75 may be applied to any suitable part of the assembly to aid in monitoring the precise position of the assembly in a body vessel.

An additional embodiment of the apparatus is illustrated in FIGS. 21–23. Catheter head 15 includes a perfusion lumen 77 bounded by a wall 78, with flow as indicated by arrows. A treatment lumen 24 is formed in a first side of wall 78 and a guide wire lumen 14 and inflation lumen 20 are formed in a second side of wall 78 opposite treatment lumen 24. A balloon 80 is bonded to the second side of wall 78 and is configured such that when balloon 80 is inflated into contact with a body vessel, treatment lumen 24 is centered in the body vessel. Perfusion lumen 77 is closed by a plug 84 proximal to balloon 80, before inlet 82 into perfusion lumen 77 (FIG. 21), to prevent fluid from passing back along catheter 12. Inflation lumen 20 is plugged by plug 86 at the distal end and has an opening 88 communicating with balloon 80 for inflation and deflation thereof.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. Apparatus for centering a radiation delivery device at a predetermined location in a body vessel, which comprises:
   an elongated tubular catheter assembly having a distal end and a proximal end;
   insertion means for inserting said distal end of said catheter into a body vessel;
   centering means adjacent to said distal end for centering said catheter in said body vessel at said predetermined location and for allowing perfusion of bodily fluids through said body vessel past said centering means and said radiation delivery device;
   said centering means comprising at least three equal sized, spaced, elongated, outwardly extending inflatable lobes on said catheter adjacent to said distal end;

a sleeve surrounding said lobes;

means for inflating said lobes;

a central lumen in said catheter;

means adapted for inserting an elongated radiation delivery device into said central lumen until said radiation device is at said predetermined site.

2. The apparatus according to claim 1 wherein said catheter further includes a guide wire lumen for receiving a guide wire for insertion of said catheter into said body vessel, an inflation lumen for passage of lobe inflation fluid and an opening between said inflation lumen and said lobes for passage of inflation fluid into said lobes.

3. The apparatus according to claim 1 wherein each of said lobes has a rounded cross section.

4. The apparatus according to claim 1 wherein each of said lobes has a cross section that is relatively narrower adjacent to said elongated tubular catheter and wider away from said elongated tubular catheter.

5. The apparatus according to claim 1 wherein said lobes run substantially parallel to said elongated tubular catheter.

6. Apparatus for centering a radiation delivery device at a predetermined location in a body vessel, which comprises:

an elongated tubular catheter assembly having a distal end and a proximal end;

insertion means for inserting said distal end of said catheter into a body vessel;

centering means adjacent to said distal end for centering said catheter in said body vessel at said predetermined location and for allowing perfusion of bodily fluids through said body vessel past said centering means and said radiation delivery device;

said centering means comprising a plurality of equal sized, spaced outwardly extending inflatable knobs each having a base on said catheter adjacent to said distal end;

reinforcing wires extending around each of said knob bases and around said catheter adjacent to each radial set of knobs;

means for inflating said knobs with a fluid;

a central lumen in said catheter;

means adapted for inserting an elongated radiation delivery device into said central lumen until said radiation device is at said predetermined site.

7. The apparatus according to claim 6 wherein said knobs extend outwardly in a plurality of radial sets of at least three knobs.

8. The apparatus according to claim 6 wherein said knobs extend outwardly in pairs, knobs in each pair lying on opposite sides of said catheter and knobs in each longitudinally succeeding pair lying at about 60 to 120° to each longitudinally preceding pair.

9. The apparatus according to claim 6 further including a sleeve over said knobs.

10. Apparatus for centering a radiation delivery device at a predetermined location in a body vessel, which comprises:

an elongated tubular catheter assembly having a distal end and a proximal end;

insertion means for inserting said distal end of said catheter into a body vessel;

centering/perfusion means adjacent to said distal end for centering said catheter in said body vessel at said predetermined location and for allowing perfusion of bodily fluids through said body vessel past said radiation delivery device;

said centering/perfusion means comprising at least three spaced torsion bars each secured at a first end to said catheter and at a second end to means for moving said second end toward and away from said first end to cause each torsion bar to bulge outwardly from said catheter when said first and second ends are brought toward each other and to lie contiguous with said catheter when said first and second ends are moved away from each other;

a sleeve over said torsion bars;

a central treatment lumen in said catheter; and means adapted for inserting a radiation delivery device into said central treatment lumen until said radiation device is at said predetermined site.

11. The apparatus according to claim 10 wherein two connected sets of said torsion bars are provided, said connected sets of torsion bars secured at a first end to said catheter and secured at a second end to said means for moving.

12. The apparatus according to claim 10 wherein a single central lumen for sequentially receiving a guide wire and for receiving a treatment device and the distal end of said catheter includes means for allowing a guide wire to pass therethrough and prevent said treatment device from passing therethrough.

\* \* \* \* \*